United States Patent
Harari et al.

(10) Patent No.: US 11,678,966 B2
(45) Date of Patent: *Jun. 20, 2023

(54) TISSUE REPAIR DEVICE AND METHOD

(71) Applicant: FEMSELECT LTD., Modi'in (IL)

(72) Inventors: Boaz Harari, Ganei-Tikva (IL); Guy Ohad, Ramat-Gan (IL)

(73) Assignee: FEMSELECT LTD, Modi'in (IL)

( * ) Notice: Subject to any disclaimer, the term of this patent is extended or adjusted under 35 U.S.C. 154(b) by 99 days.

This patent is subject to a terminal disclaimer.

(21) Appl. No.: 17/368,829

(22) Filed: Jul. 7, 2021

(65) Prior Publication Data

US 2021/0401561 A1 Dec. 30, 2021

Related U.S. Application Data

(63) Continuation of application No. 15/316,698, filed as application No. PCT/IL2015/050585 on Jun. 10, 2015, now Pat. No. 11,076,943.

(Continued)

(51) Int. Cl.
*A61F 2/00* (2006.01)
*A61B 17/04* (2006.01)
(Continued)

(52) U.S. Cl.
CPC .............. *A61F 2/0045* (2013.01); *A61B 8/12* (2013.01); *A61B 17/0401* (2013.01); *A61B 17/06109* (2013.01); *A61B 17/06166* (2013.01); *A61B 17/3403* (2013.01); *A61F 2/0063* (2013.01); *A61F 6/12* (2013.01); *A61B 2017/00438* (2013.01); *A61B 2017/00805* (2013.01);

(Continued)

(58) Field of Classification Search
CPC ........ A61F 2/0045; A61F 2/0063; A61F 6/12; A61F 2002/0072; A61B 8/12; A61B 17/0401; A61B 17/06109; A61B 17/06166; A61B 17/3403; A61B 2017/00438; A61B 2017/00805; A61B 2017/0409; A61B 2017/0464; A61B 2017/3413
See application file for complete search history.

(56) References Cited

U.S. PATENT DOCUMENTS 6,066,104 A 5/2000 Dao et al.
6,332,888 B1 12/2001 Levy et al.
(Continued)

FOREIGN PATENT DOCUMENTS

CA 2093824 10/1994
DE 2910410 12/1979
(Continued)

OTHER PUBLICATIONS

An Office Action dated Dec. 23, 2021, which issued during the prosecution of Canadian Patent Application No. 2,951,506.
(Continued)

*Primary Examiner* — Peter Luong
(74) *Attorney, Agent, or Firm* — McDonnell Boehnen Hulbert & Berghoff LLP

(57) ABSTRACT

A surgical device is provided. The surgical device includes a housing adapted for mounting on a finger of a user; and at least one guide tube attached along a length of the housing. The guide tube is configured for guiding a tissue repair implant from a proximal opening to a distal opening thereof.

15 Claims, 16 Drawing Sheets

Related U.S. Application Data

(60) Provisional application No. 62/009,946, filed on Jun. 10, 2014.

(51) Int. Cl.
  *A61B 17/06* (2006.01)
  *A61F 6/12* (2006.01)
  *A61B 8/12* (2006.01)
  *A61B 17/34* (2006.01)
  *A61B 17/00* (2006.01)

(52) U.S. Cl.
  CPC ............... *A61B 2017/0409* (2013.01); *A61B 2017/0464* (2013.01); *A61B 2017/3413* (2013.01); *A61F 2002/0072* (2013.01)

(56) References Cited

U.S. PATENT DOCUMENTS

| | | |
|---|---|---|
| 6,506,190 B1 | 1/2003 | Walshe |
| 8,257,366 B2 | 9/2012 | Schneider et al. |
| 8,535,216 B2 | 9/2013 | Chu et al. |
| 8,617,183 B2 | 12/2013 | Schneider et al. |
| 9,451,944 B2 | 9/2016 | Schneider et al. |
| 9,517,058 B2 | 12/2016 | Harari et al. |
| 9,737,391 B2 | 8/2017 | Harari et al. |
| 11,076,943 B2 | 8/2021 | Harari et al. |
| 2001/0041914 A1 | 11/2001 | Frazier et al. |
| 2002/0077631 A1 | 6/2002 | Lubbers et al. |
| 2005/0250987 A1 | 11/2005 | Ewers et al. |
| 2006/0047285 A1 | 3/2006 | Fields |
| 2007/0142846 A1 | 6/2007 | Catanese, III et al. |
| 2007/0239208 A1 | 10/2007 | Crawford |
| 2009/0216075 A1 | 8/2009 | Bell et al. |
| 2010/0030237 A1* | 2/2010 | Hayashi ............. A61B 17/0401 606/144 |
| 2010/0274074 A1 | 10/2010 | Khamis et al. |
| 2011/0092985 A1 | 4/2011 | Gaynor et al. |
| 2011/0092991 A1 | 4/2011 | Gaynor et al. |
| 2011/0929186 | 4/2011 | Gaynor et al. |
| 2011/0196389 A1 | 8/2011 | Schneider et al. |
| 2012/0123410 A1 | 5/2012 | Craig |
| 2014/0100580 A1 | 4/2014 | Yu et al. |
| 2015/0320442 A1 | 11/2015 | Harari et al. |
| 2016/0235461 A1 | 8/2016 | Sumko |
| 2017/0196671 A1 | 7/2017 | Harari et al. |
| 2019/0029042 A1 | 9/2019 | Dougherty |

FOREIGN PATENT DOCUMENTS

| | | |
|---|---|---|
| DE | 10321012 | 12/2004 |
| EP | 1862134 | 5/2007 |
| EP | 2870921 | 5/2013 |
| JP | 2004-509685 | 4/2004 |
| JP | 2008-510589 | 4/2008 |
| JP | 2008-523926 | 7/2008 |
| KR | 101115493 | 3/2012 |
| WO | 95/14438 | 6/1995 |
| WO | 2011/047685 | 4/2011 |
| WO | 2012/047626 | 4/2012 |
| WO | 2013/093924 | 6/2013 |
| WO | 20151189843 | 12/2015 |

OTHER PUBLICATIONS

An Office Action together with an English summary dated Jan. 27, 2022, which issued during the prosecution of Korean Patent Application No. 10-2017-7000766.
An English summary of an Office Action dated Feb. 16, 2022 which issued during the prosecution of Chinese Patent Application No. 201680092073.5.
An Office Action dated May 30, 2022, which issued during the prosecution of Canadian Patent Application No. 3,046,184.
An Office Action dated May 25, 2022, which issued during the prosecution of U.S. Appl. No. 16/468,379.
An Office Action dated Aug. 13, 2021, which issued during the prosecution of Indian Patent Application No. 201947028179.
An Office Action dated Nov. 29, 2021, which issued during the prosecution of U.S. Appl. No. 16/468,379.
Rofaeel, A., M.D., Peng, Philip, M.B.B.S., F.R.C.P.C., Louis, I., M.D., & Chan, Vincent, M.D., F.R.C.P.C. (2008). Feasibility of real-time ultrasound for pudendal nerve block in patients with chronic perineal pain. Regional Anesthesia and Pain Medicine, 33(2), 139-45.
U.S. Appl. No. 62/009,946, filed Jun. 10, 2014.
The Extended European Search Report for EP 16923881.3, dated Jun. 24, 2020, pp. 1-10.
An Office Action dated Jan. 23, 2019, which issued during the prosecution of U.S. Appl. No. 15/651,472.
Notice of Allowance dated Jun. 19, 2018, which issued during the prosecution of US Patent Application No. 141667 954.
An Office Action dated Nov. 15, 2017, which issued during the prosecution of US Patent Annlication No. 141667 954.
An English translation of an Office Action dated Oct. 10, 2017 which issued during the prosecution of Jananese Patent Annlication No. 2016-572283.
An International Search Report and a Written Opinion both dated Mar. 17, 2017, which issued during the prosecution of Applicant's PCTIIL2016/051338.
The International Search Report {ISR) with Written Opinion for PCT/IL2015/050585 dated Oct. 2, 2015, pp. 1-16.
An Office Action dated Oct. 21, 2022, which issued during the prosecution of U.S. Appl. No. 16/468,379.
An Office Action together with the English Summary dated Dec. 23, 2022 which issued during the prosecution of Japanese Patent Application No. 201680092073.5.

* cited by examiner

TISSUE REPAIR DEVICE AND METHOD

CROSS-REFERENCE TO RELATED APPLICATION

This application is a continuation of U.S. patent application Ser. No. 15/316,698, filed Dec. 6, 2016, which is a U.S. National Stage application of International Patent Application No. PCT/IL2015/050585 filed Jun. 10, 2015, which claims priority to U.S. Provisional Application No. 62/009,946 filed Jun. 10, 2014, which are all hereby incorporated by reference in their entirety.

FIELD AND BACKGROUND OF THE INVENTION

The present invention relates to a device and method for guiding and anchoring an implant to a tissue. Embodiments of the present invention relate to a device and method for guiding and anchoring a suture, suture anchor or mesh in a sacrospinous ligament for the purpose of repairing a pelvic floor disorder pelvic organ prolapse (POP).

Trans-vaginal pelvic floor repair is a surgical procedure which utilizes blunt tissue dissection to provide access to the sacrospinous ligament from the posterior vaginal wall. A sling or mesh is then anchored to the sacrospinous ligament and the vaginal apex or the uterine isthmical fibrotic ring, cervix or body, to thereby support prolapsing tissues and/or organs.

Although pelvic floor repair is a common procedure, access to the sacrospinous ligament is typically effected by improvised manual blunt dissection techniques and/or use of off the shelf instruments.

Centro-apical reconstruction is key for proper pelvic organ prolapse (POP) repair. The premium supportive pelvic structure is the sacrospinous ligament (SSL) which is positioned at the posterior aspect of the pelvis. The SSL is a robust ligament and thus provides a long lasting solution. Since it is positioned high in the pelvis and medially the SSL provides a level 1 support (DeLancey) and reduces the likelihood of dyspareunia when utilized for prolapse repair.

Vaginal wall access to the SSL can be difficult and hazardous since organs and tissues surrounding the access path can easily be injured during dissection. Present day approach for accessing the SSL starts with an incision at the mid-line of the posterior or anterior vaginal wall followed by lateral dissection under the sub-mucosal fascia to the pelvic side wall and dissection towards the ischial spine to the mid SSL (MSSL).

This approach decreases risk of tissue injury by bypassing the bladder/rectum while maintaining accurate navigation along the above mentioned landmarks. Such an approach requires a high degree of skill and as such can lead to a high rate of complications.

While reducing the present invention to practice, the present inventors have developed a device which can be used to deliver a tissue anchor to anatomical landmarks and structures such as the ischial spine and the sacrospinous ligament from the vaginal cavity.

SUMMARY OF THE INVENTION

According to one aspect of the present invention there is provided a surgical device comprising: a housing adapted for mounting on a finger of a user; and (b) at least one guide tube attached along a length of the housing, the at least one guide tube being configured for guiding a tissue repair implant from a proximal opening to a distal opening thereof.

According to further features in preferred embodiments of the invention described below, the guide tube is attached to the housing such that the proximal opening protrudes beyond a proximal end of the housing.

According to still further features in the described preferred embodiments the guide tube is attached to the housing such that the proximal opening is positioned above a back of a hand of the user when the housing is mounted on the finger.

According to still further features in the described preferred embodiments the housing is configured so as to enable the user to palpate the tissue via the finger attached to the housing.

According to still further features in the described preferred embodiments the housing is open at a distal end thereof.

According to still further features in the described preferred embodiments the guide tube is attached to the housing such that the distal opening abuts the tissue when the finger of the user contacts the tissue.

According to still further features in the described preferred embodiments the guide tube is attached to the housing such that the distal opening is displaced from the tissue when the finger of the user contacts the tissue.

According to still further features in the described preferred embodiments the suture end is attached to an anchor.

According to still further features in the described preferred embodiments the housing is configured for enabling flexion of the finger at a distal and/or proximal interphalangeal joint.

According to still further features in the described preferred embodiments the housing is configured for attaching an imaging device thereto.

According to still further features in the described preferred embodiments the imaging device is an ultrasound transducer.

According to still further features in the described preferred embodiments an imaging head of the ultrasound transducer is capable of abutting the tissue when the ultrasound transducer is attached to the housing.

According to still further features in the described preferred embodiments the imaging head abuts the tissue when the finger attached to the housing contacts the tissue.

According to still further features in the described preferred embodiments the tissue is a posterior-lateral vaginal wall and the housing is configured for delivery into the vaginal canal via the finger.

According to still further features in the described preferred embodiments when the housing is positioned within the vaginal canal with the finger in contact with the posterior-lateral vaginal wall, the proximal opening of the at least one guide tube extends out of the vaginal canal.

According to still further features in the described preferred embodiments the tissue repair implant is a mesh, a sling, a suture or a suture-anchor.

According to another aspect of the present invention there is provided a method of repairing a pelvic floor disorder comprising: (a) positioning a surgical device via a finger within a vaginal cavity, the surgical device including a housing adapted for mounting on the finger and at least one guide tube attached along a length of the housing; (b) using the finger to palpate a posterior-lateral wall of the vaginal cavity and locate a sacrospinous ligament therethrough; and (c) advancing a tissue repair implant through the at least one guide tube and through a posterior-lateral wall to thereby anchor the tissue repair implant to the sacrospinous ligament.

According to still further features in the described preferred embodiments the tissue repair implant is a mesh, a sling, a suture or a suture-anchor.

According to still further features in the described preferred embodiments the device further includes an ultrasound transducer attached to the housing and further wherein (b) is effected under ultrasound guidance.

According to still further features in the described preferred embodiments the guide tube is attached to the housing such that a proximal opening of the guide tube is positioned outside the vaginal cavity.

According to another aspect of the present invention there is provided a method of repairing a pelvic floor disorder comprising (a) positioning a surgical device via a finger within a vaginal cavity, the surgical device including a housing adapted for mounting on the finger and at least one guide tube attached along a length of the housing; (b) using the finger to palpate a posterior-lateral wall of the vaginal cavity and locate a sacrospinous ligament therethrough; (c) advancing a suture-anchor through the at least one guide tube and through a posterior-lateral wall to thereby anchor the suture-anchor to the sacrospinous ligament; and (d) advancing a mesh over at least one suture thread of the suture-anchor; and (e) tying the at least one suture thread to secure the mesh in position.

According to another aspect of the present invention there is provided a device for delivering a mesh to an intrabody location using a suture anchor as a guide and the method described above. The device includes a hollow tube for accepting one or more suture threads, and a distal end for accepting a releasable cuff attached to the mesh.

The present invention successfully addresses the shortcomings of the presently known configurations by providing a device and method for tissue repair from within a body cavity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
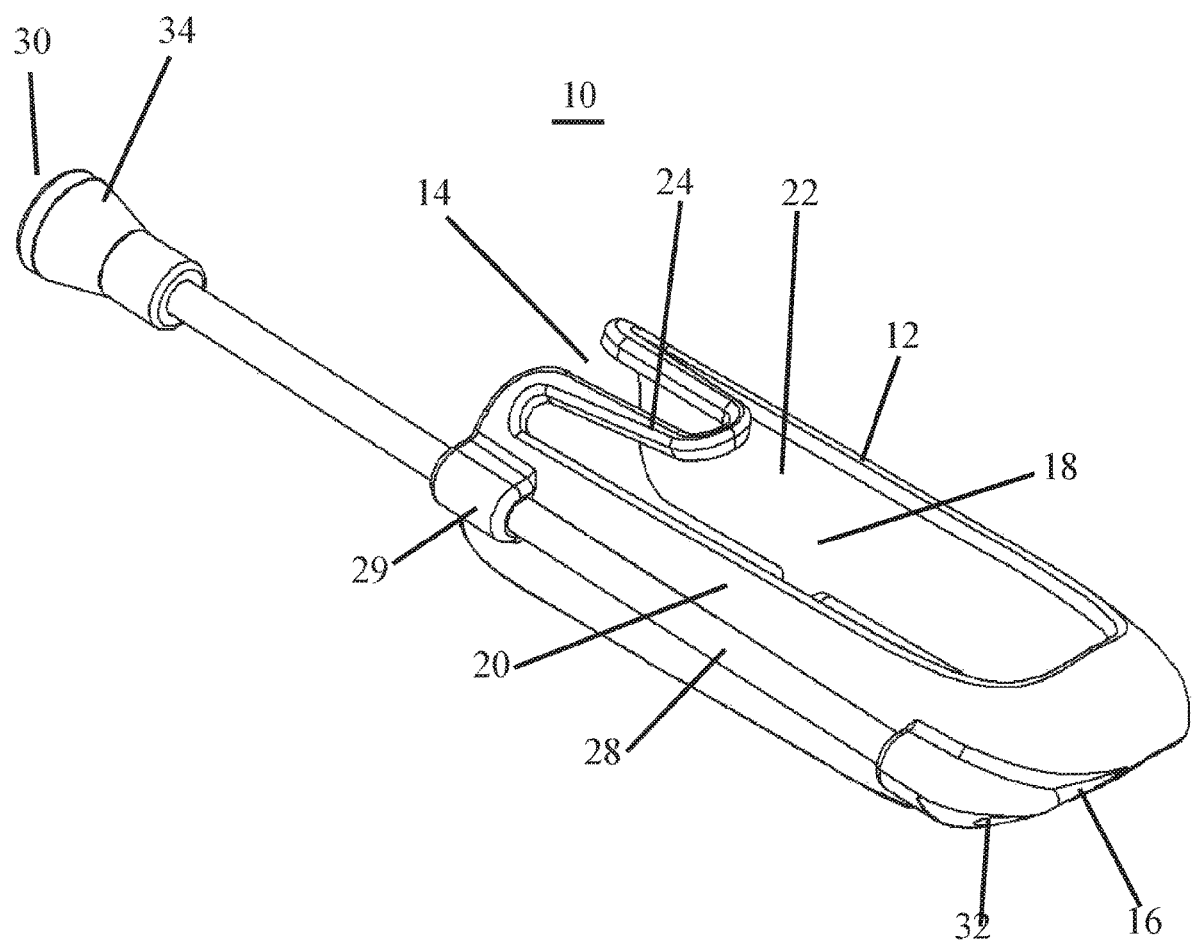
FIG. 1 illustrates an embodiment of the present device having a single guide tube.

The present invention is of a device which can be used for tissue repair, and specifically of a finger mounted device which can be used to deliver a tissue repair implant through a wall of a body cavity.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Pelvic organ prolapse (POP), and especially apical central supportive defect (ACSD), significantly affects the quality of life of about 20% of the female population.

POP is typically corrected via a transabdominal or a transvaginal surgical procedure.

The transvaginal reconstruction approach is regarded as superior to the transabdominal approach due to a shorter operative time and hospital stay and quicker rehabilitation. However, transvaginal procedures require advanced surgical skill and as such are performed by a rather small and highly qualified group of surgeons.

In the transvaginal procedure, a surgeon can elect to suspend the vaginal apex (VA) or the uterine cervix (UC) to the sacrospinous-ligament (SSL), sacrum, arcus tendineus fascia pelvis (ATFP) or other potentially solid supportive pelvic structures, which are accessed via anterior or posterior vaginal wall incisions and blunt dissection of tissues.

Creating an access path to these tissues is a major challenge of transvaginal procedures since it requires complicated navigation to the pelvic side wall (PSW), ischial spine (IS) and then to the mid SSL (MSSL) or the sacrum which carries with it a risk of damaging the bladder, rectum, blood vessels, nerves, ureters, etc.

Most POP procedure complications are attributed to the dissection necessary to create the tissue path to the elected tissue support site.

In order to traverse these limitations of prior art transvaginal procedures, the present inventors have devised an approach which utilizes a finger mounted intravaginal device which enables the surgeon to palpate the SSL and deliver a tissue repair implant thereto.

As used herein, the phrase "pelvic floor disorder" refers to any disorder of the pelvic floor that is associated with prolapse, herniation or incorrect anatomical positioning of pelvic floor tissues.

Thus, according to one aspect of the present invention there is provided a device for tissue repair, and in particular, repair of pelvic floor disorders. The term "repair" when used herein with reference to pelvic floor disorders refers to correction (complete or incomplete) of anatomy, via, a tissue repair implant such as a suture, suture anchor, mesh, sling and/or the like.

The present device includes a housing adapted for mounting on a finger of a user, preferably an index finger of the user. The housing can be configured for mounting over the finger tip or any portion of the finger (up to the distal or proximal interphalangeal joint or the entire finger). The device further includes at least one guide tube (preferably 1 or 2) attached along a length of the housing. Thus, the guide tube runs parallel or substantially parallel to the finger of the user when the housing is mounted thereupon.

The housing is substantially 'finger'-shaped (elongated slightly compressed cylinder) with a longitudinal lumen mountable over a finger and smooth external walls (optionally having longitudinal apertures) for facilitating insertion of the housing into a body cavity (e.g. vaginal or anal cavity) when mounted over the finger. The distal end (away from user) includes an opening for the tip of the finger, such opening can be covered by an elastic this membrane.

The housing can be fabricated from a polymer or alloy (preferably biocompatible) using molding or machining approaches. Typical dimensions for housing are 65 mm length, and 18 mm internal diameter. The housing includes a finger adjusting and retaining mechanism in order to ensure that the housing securely mounts onto a finger of any length or diameter without inadvertently detaching. Such a mechanism can include an elastic tab mounted within the housing lumen or an adjustment mechanism for adjusting the length, height and/or width (or diameter) of the housing. One example of such a mechanism is described below with reference to the Figures.

The guide tube(s) is attached to the housing or co-fabricated therewith and is configured for guiding an implant from a proximal opening to a distal opening thereof.

The guide tube is preferably attached along a side of the housing such that its runs along a side of a finger (when the hand is viewed from the top). A detailed description of one embodiment of the present device is provided hereinbelow with reference to FIGS. 1-8.

As is mentioned hereinabove, the device of the present invention can be used for tissue repair by enabling delivery of a tissue repair implant from the guide tube. Such guiding can be effected with or without imaging guidance. When performed under imaging, the present device is configured for attaching an imaging device thereto. One example of an imaging device is an ultrasound transducer which can be attached to a dedicated bracket provided on the housing.

The present device can further include irrigation lumens for attaching an irrigation source and/or suction.

Referring now to the drawings, FIGS. 1-8 illustrate the present device which is referred to herein as device 10. Device 10 is configured for intravaginal access and pelvic floor repair, however, it should be noted that device 10 can be modified for access into other body cavities such as the anal canal to affect repair therein or therethrough.

Device 10 includes a housing 12 which is substantially finger shaped and is 6 cm in length and 1.8 cm in diameter. Housing can be fabricated from plastic, metal or a rubber like material. Housing 12 is configured for mounting over an entire index finger (see FIG. 5) but will also provide the required functionality if configured for mounting over a portion of this finger. Mounting can be over a naked finger or one covered by a surgical glove. Housing 12 includes a proximal opening 14 and distal opening 16 forming lumen 18 surrounded by walls 20. Walls 20 can include several apertures 22 (top aperture 22 shown) and a finger retaining mechanism 24 for elastically engaging the finger (FIG. 5) to ensure that housing 12 is retained on a finger regardless of its dimensions. Finger retaining mechanism 24 can be designed to accommodate any finger size by providing an accommodative elastic force (downward) on the finger surface. Such a force would be enough to trap the finger within housing but would still enable a user to remove the housing by sliding it off the finger. The diameter of the index finger distal phalanx ranges between 13-18 mm for most individuals and thus a single design can be used to accommodate such a finger size range.

Distal opening 16 is sized and configured to enable a tip of the finger to protrude therethrough when housing 12 is mounted ion a finger. This enables a user to palpate tissue wall when device 10 is in use and positioned within the vaginal cavity. Distal opening 16 can be covered by a thin elastic membrane that enables palpation and yet provides a barrier between the user's finger from the tissue in cases where the user is not wearing gloves.

Figure 2:
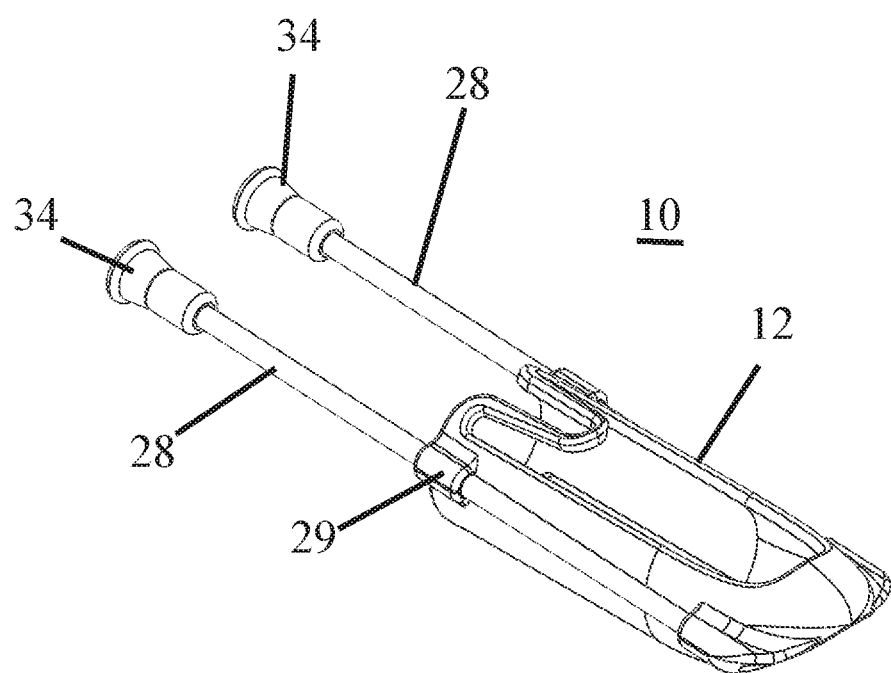
FIG. 2 illustrates an embodiment of the present device having two guide tubes.
Figure 6:
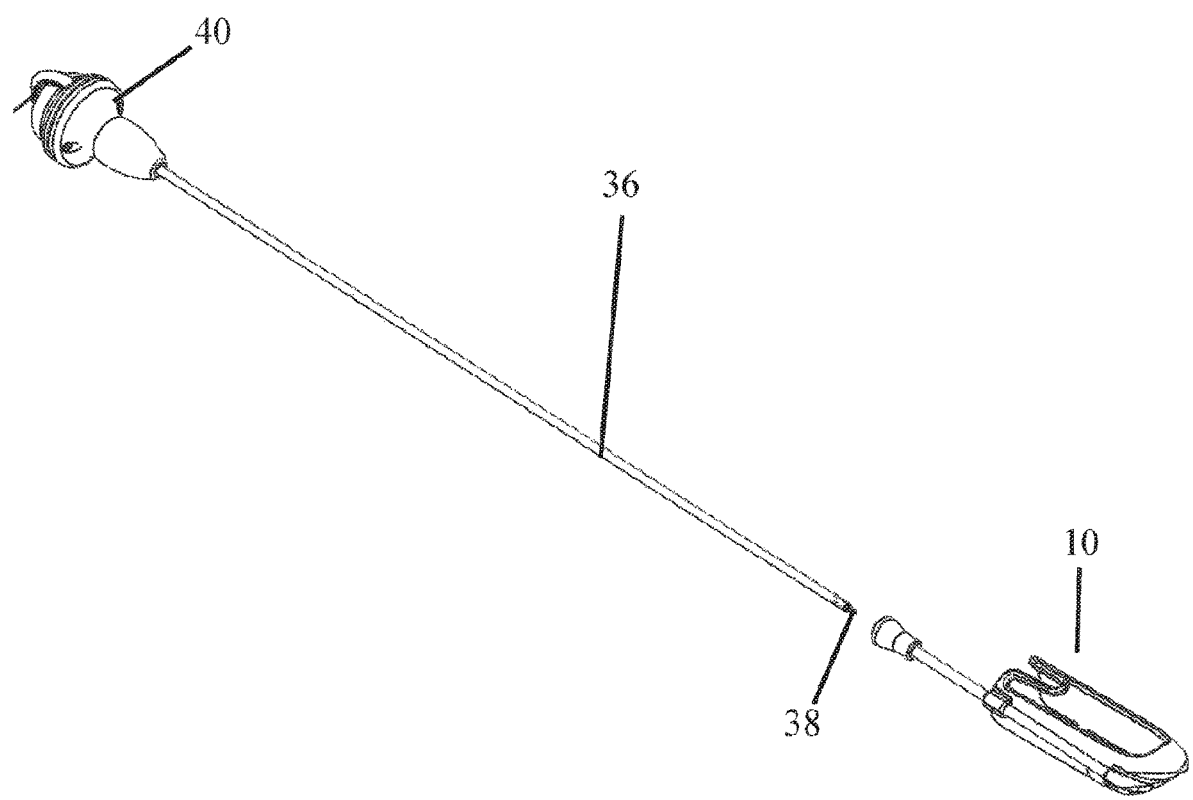
FIGS. 6-7 illustrate insertion of the implant delivery device into the guide tube.
Figure 7:
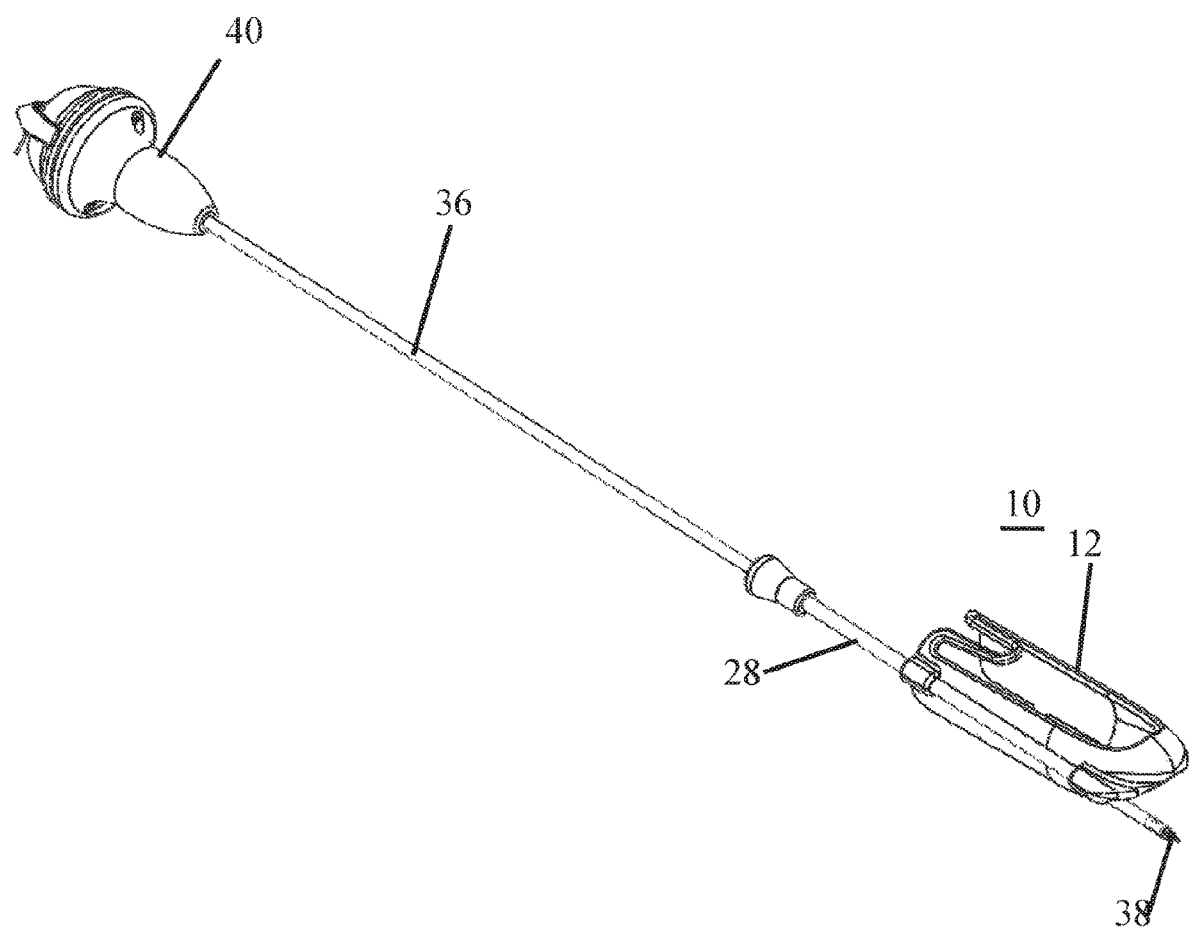
Figure 8:
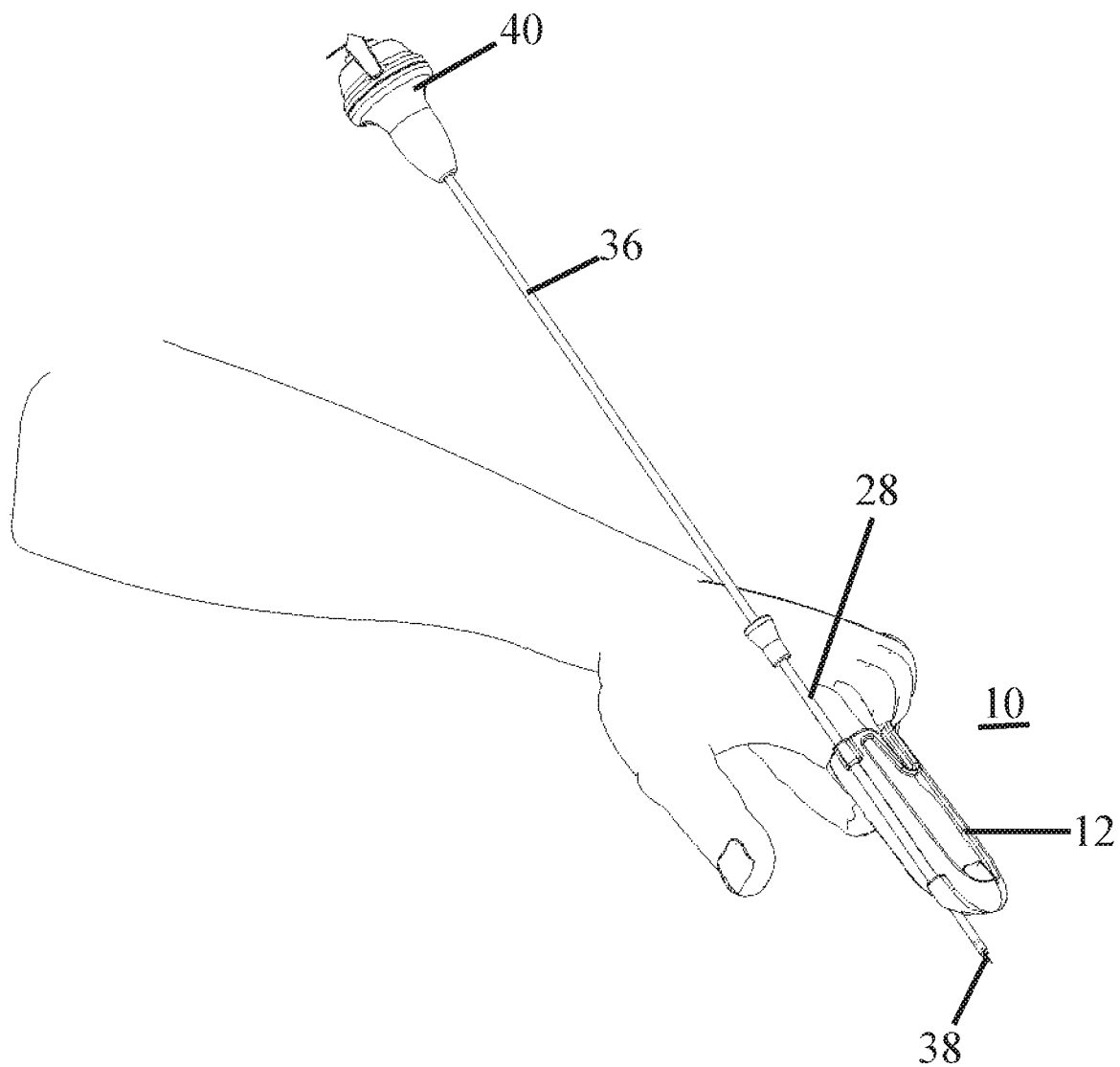
FIG. 8 illustrates the device of FIG. 1 mounted on a finger with the implant delivery device positioned within the guide tube.

Device 10 further includes at least one guide tube 28 (1 shown in FIG. 1, 2 shown in FIG. 2) Guide tube can be attached to housing 12 via brackets 29 (shown in FIGS. 1-2). Guide tube 28 is configured as elongated tube having proximal and distal openings (30 and 32 respectively). Guide tube 28 has a length greater than that of housing 12 such that when housing 12 is positioned within the vaginal cavity (with distal opening at or near the lateral posterior wall), proximal opening 30 is positioned outside the vaginal cavity to allow access and delivery of a tissue repair implant therethrough (as is shown in FIGS. 6-8). The length of guide tube 28 can be anywhere from 70-120 mm, while the outer and inner diameter can be anywhere from 2-8 mm and 1-3 mm (respectively). Guide tube 28 can be fabricated from a substantially rigid material such as stainless steel or from an elastic material such as Nitinol or a polymer such as Polycarbonate. An elastic embodiment of guide tube 28 can be advantageous in cases where the distal opening of the tube is not aligned with the proximal opening.

Guide tube 28 includes a port 34 for allowing a delivery device 36 (shown in FIGS. 6-8) to easily access the lumen of guide tube 28.

Delivery device 36 can be constructed from two coaxial tubes. An Internal tube attached to a tissue anchor 38 (shown in FIG. 6) and an external rigid tube which is coaxially disposed around the first tube. The tissue anchor 38 (which can be attached to a suture, mesh or sling) can be delivered from the rigid tube by advancing the first tube therewithin. To effect such delivery, delivery device 36 includes a handle 40 for actuating forward movement (in a distal direction) of the first tube within the rigid tube. Delivery device 36 is preferably capable of puncturing the vaginal wall and driving tissue anchor 38 through the tissue and into the target site (e.g. MSSL). As such, the distal end of the first tube can be configured for tissue puncturing (beveled, double beveled or conical). Alternatively, tissue anchor 38 can be configured for tissue puncturing or still alternatively an initial incision in the vaginal wall can be used to deliver the first tube therethrough. The first and rigid tubes or anchor 38 can include an imaging marker for identifying these elements within an imaging plane. An example of an echogenic marker which can be used along with an ultrasound probe is provided in U.S. 20050228288.

As is shown in FIG. 2, device 10 of the present invention can include 2 guide tubes 28. Such a configuration allows a user to choose the best side for delivery of a tissue repair implant or to deliver two implants.

Figure 3:
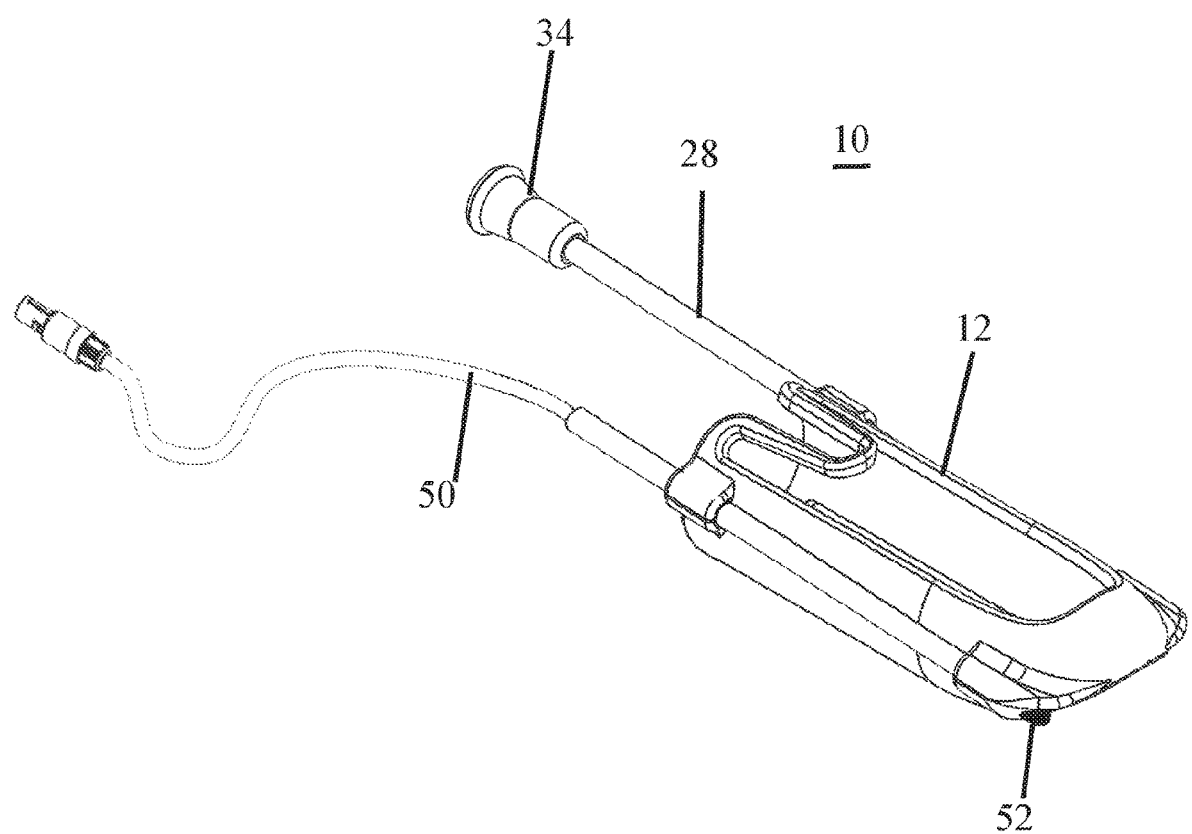
FIG. 3 illustrates an embodiment of the present device having a single guide tube and an imaging device.
Figure 4:
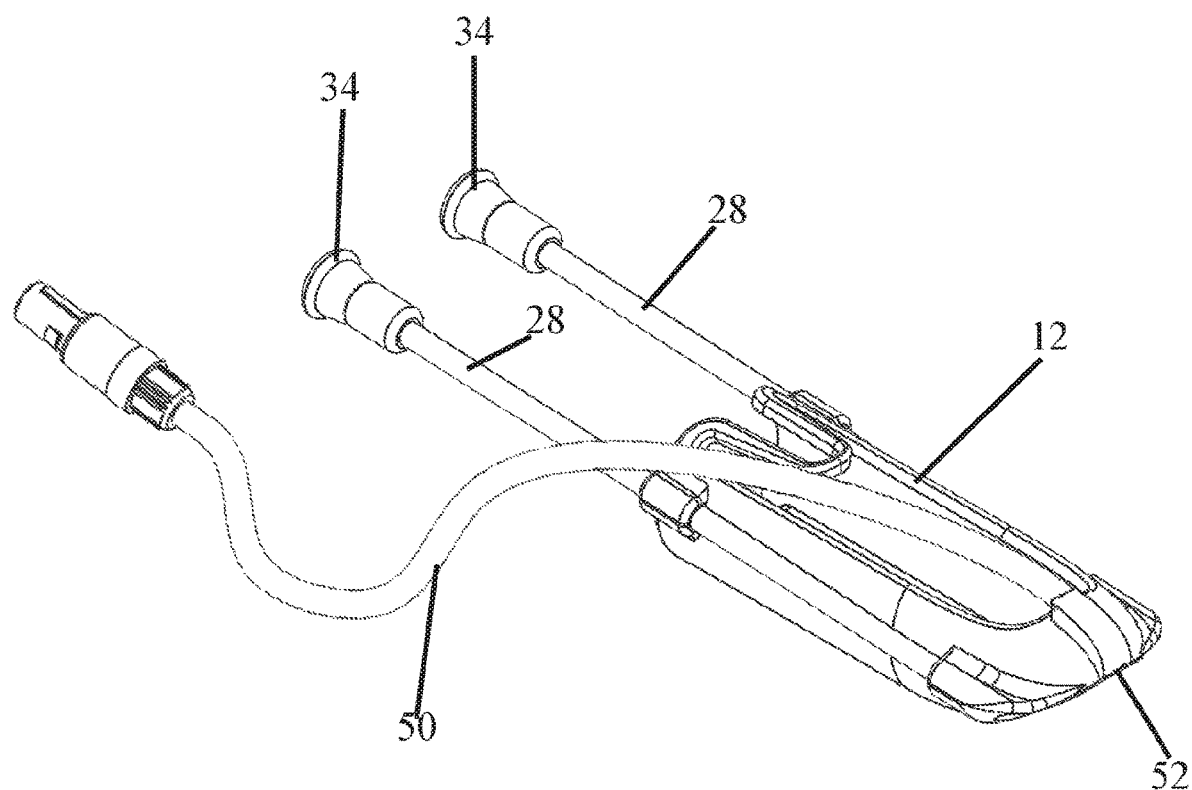
FIG. 4 illustrates an embodiment of the present device having two guide tubes and an imaging device.
Figure 5:
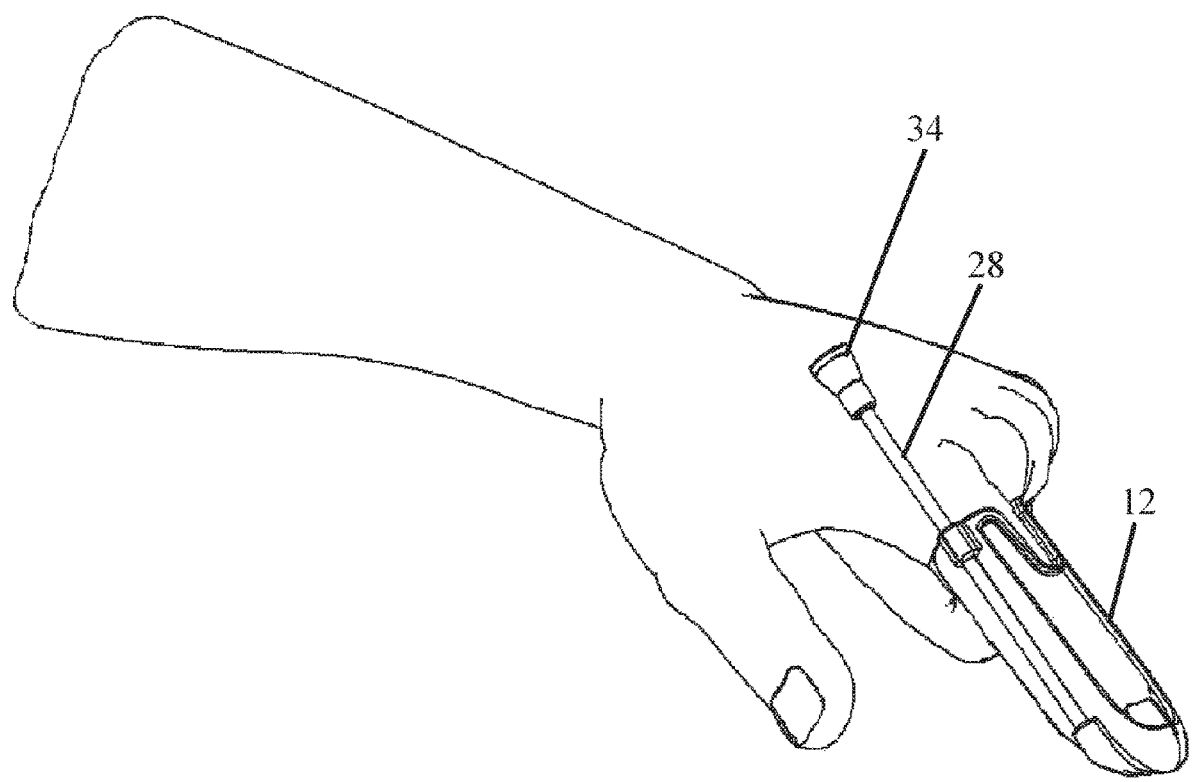
FIG. 5 illustrates the device of FIG. 1 mounted on a finger of a user.

As is shown FIG. 3, device 10 can also include an imaging device 50 which is attached to housing 12 with an imaging head 52 positioned at a distal end of house 12 on a side opposite of guide tube 28 distal opening 32 or in the middle, as is shown in FIG. 4 (which depicts a device 10 having two guide tubes 28 and an imaging device 50). One example of an imaging device which can be used in device 10 is an ultrasound imaging device. An ultrasound imaging device having a transducer head positioned at the distal end of housing near distal opening 32 of guide tube 28 can be used to image the SSL and surrounding structures/organs and provide additional guidance for delivery of the tissue repair implant.

Device 10 of the present invention can be used in a pelvic organ prolapse (POP) repair procedure as follows.

The site of anchoring is selected based on pre-palpation and/or pre-procedure vaginal US.

The present device is positioned on an index finger of a dominant hand and a delivery device (needle) is positioned within the guide tube such that a distal end of the external rigid tube of the delivery device is flush with the distal opening of the guide tube.

The present device is introduced into the vaginal cavity and the index finger tip is used to palpate the tissue target through the vaginal wall. The external rigid tube of the delivery device is then pressed against the vaginal wall at the region of the ligament.

The internal tube of the delivery device is then actuated via the delivery button of the handle to deliver the anchor through the vaginal wall and into the ligament. The internal tube is then withdrawn leaving the anchor and attached suture/mesh in position. The suture end(s) are secured outside the vaginal cavity via forceps and the initial pull out force is verified by manually pulling on the suture ends. Optionally, the procedure is then repeated for the second side of the device thereby attaching a second anchor-suture/mesh to the ligament at a second site.

The suture ends are then attached to the uterine cervix fibrotic ring, the serosa of the vaginal apex, the utero-sacral ligaments, the vagina (in post hysterectomy subjects), or any other appropriate centro-apical anchoring point of the pelvic floor as is routine for prolapse procedures.

As is described hereinabove, the present device can also be used to deliver a mesh to the anchoring site. FIGS. 9a-h illustrate delivery of a mesh to the anchoring site using the suture anchor implanted by the present device as a guide.

Figure 9A:
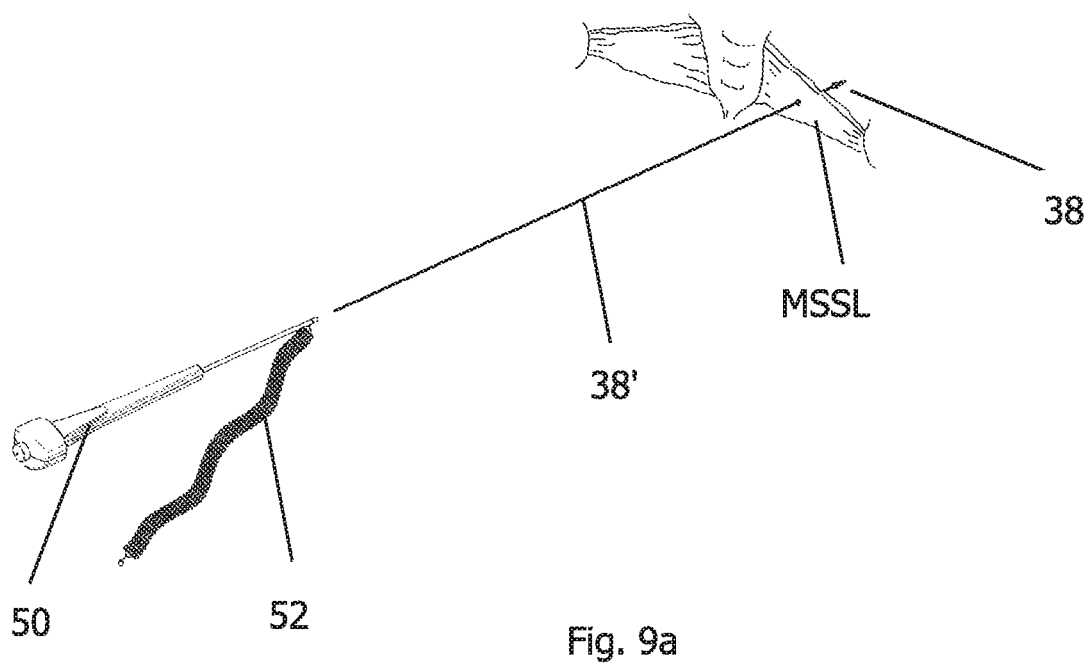
FIGS. 9a-h illustrate mesh delivery and securement using the suture-anchor delivered by the present device as a guide.
Figure 9B:
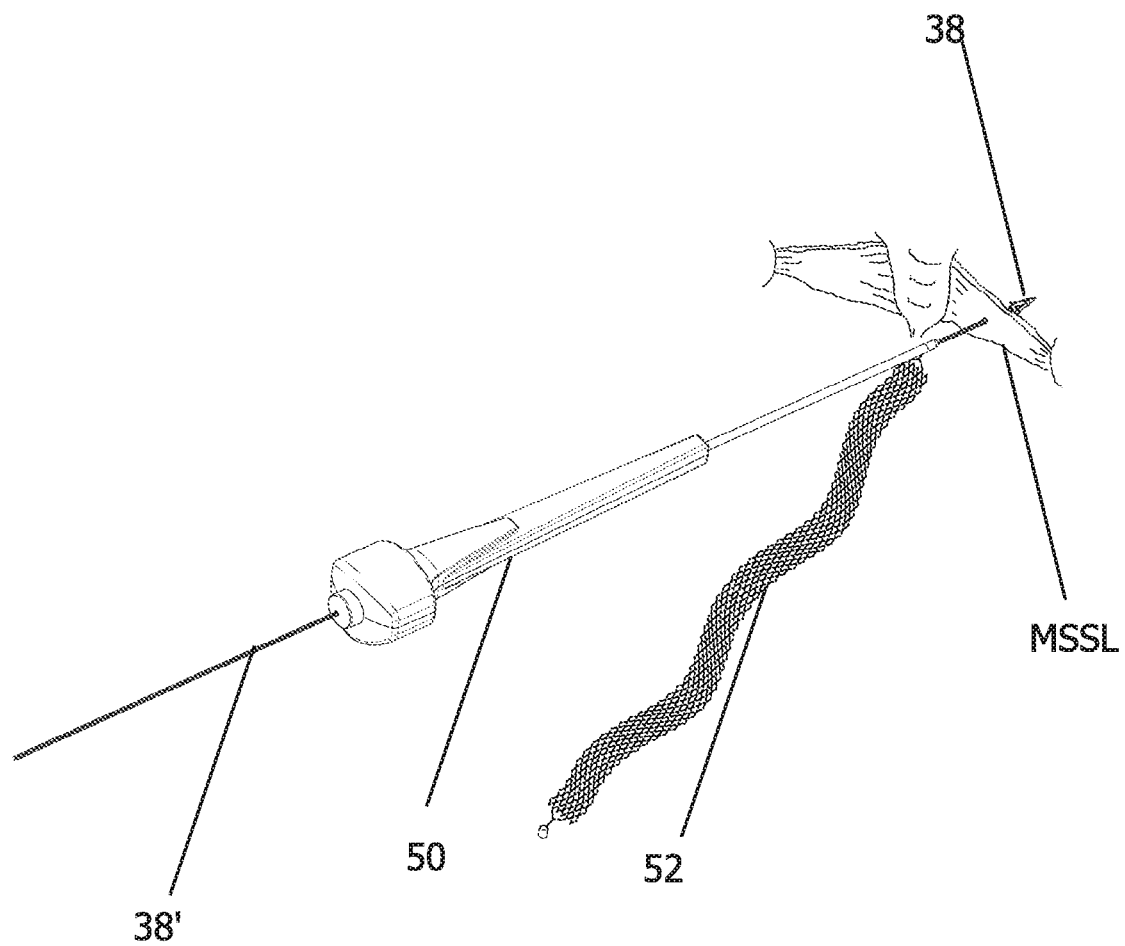
Figure 9C:
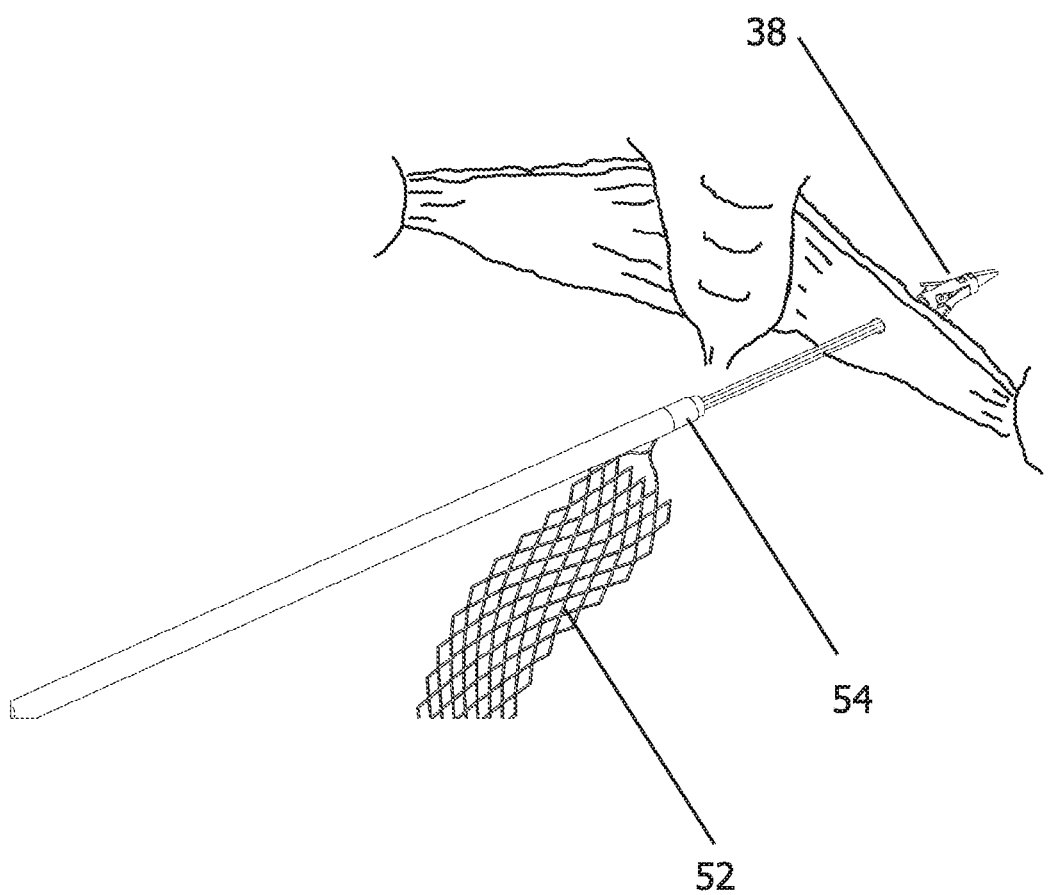
Figure 9D:
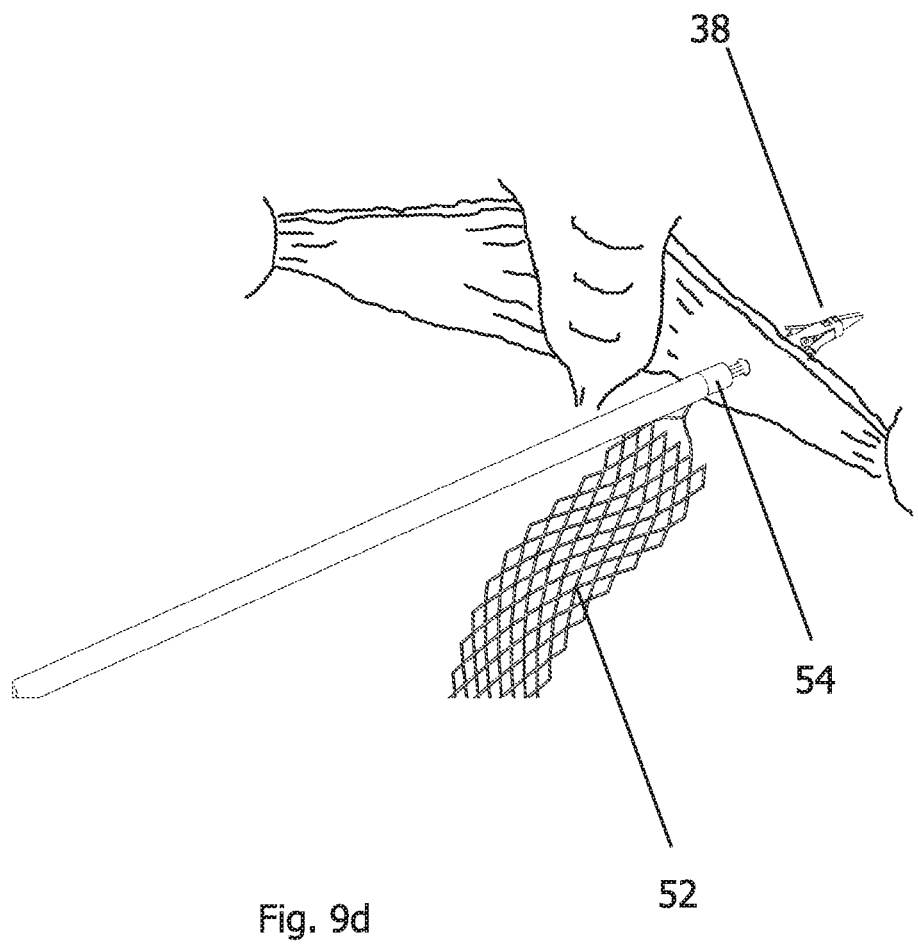
Figure 9E:
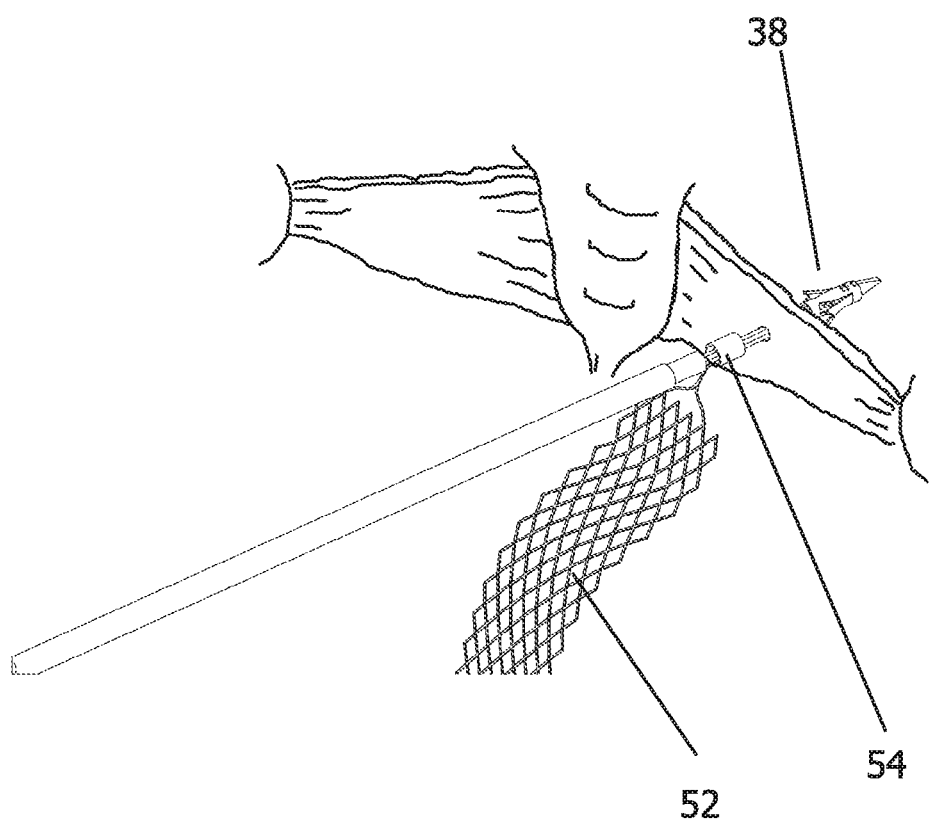

FIG. 9a illustrates anchor 38 positioned through the MSSL and attached to a suture 38'.

A mesh delivery device 50 carrying mesh 52 having a distal cuff 54 (FIG. 9e) are threaded over one or both sutures 38'. Device 50 and attached cuff 54 are advanced over suture thread(s) (FIGS. 9b-d) by pushing device handle from outside the vaginal canal.

Figure 9F:
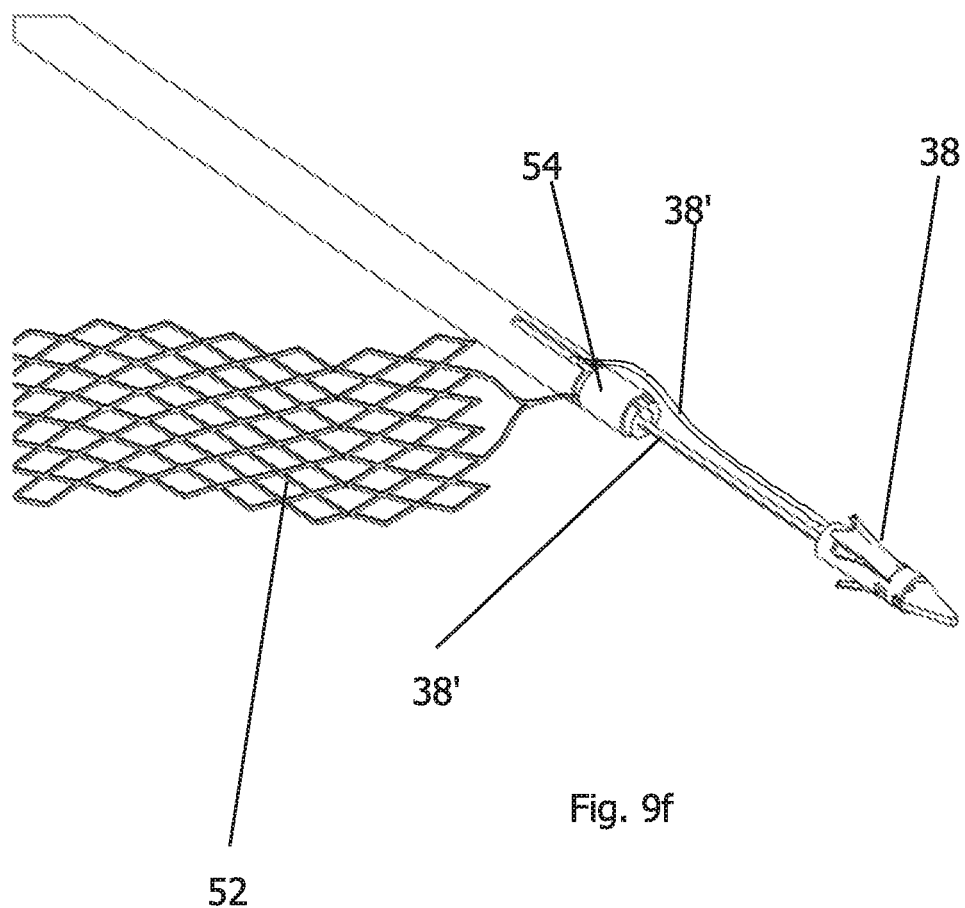
Figure 9G:
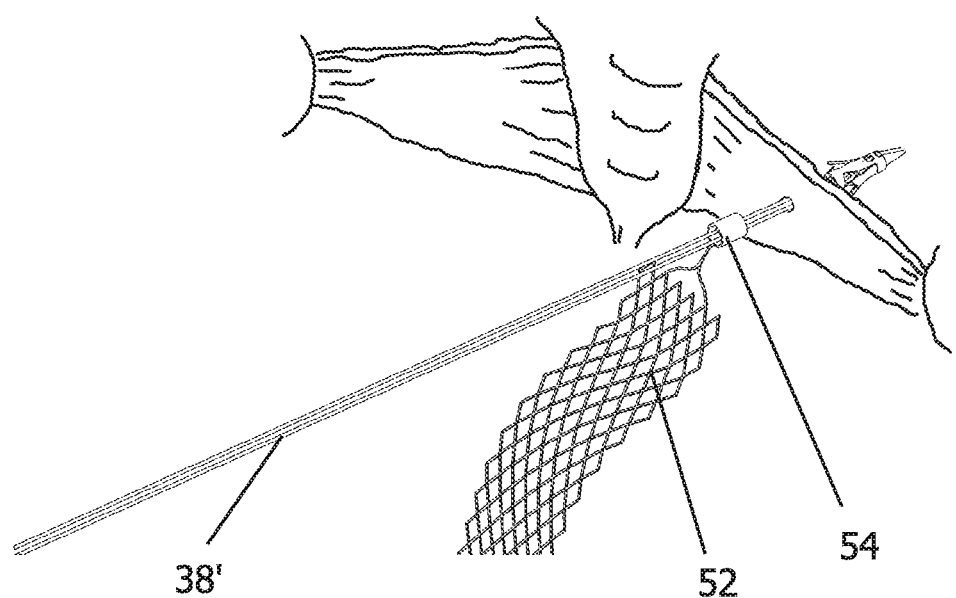
Figure 9H:
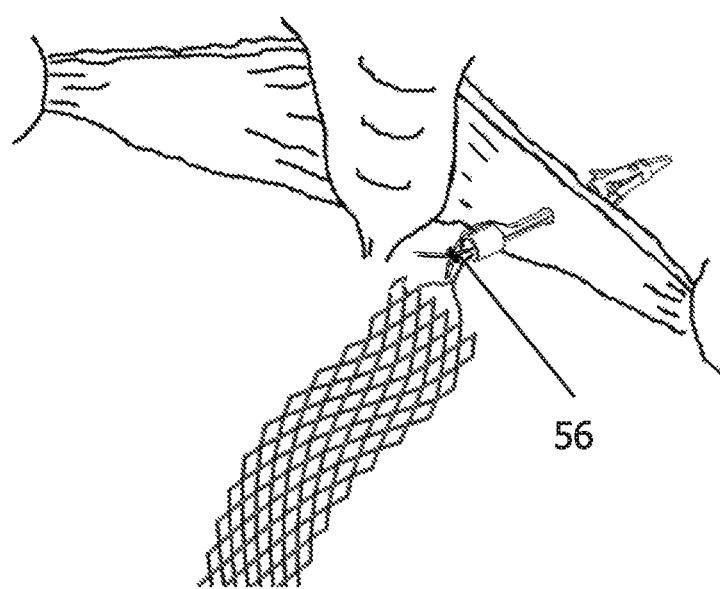

Cuff 54 is attached to the distal end of mesh 52 and is positioned around the tip of device 50. Cuff 54 can be fabricated from an alloy or polymer and can be configured to elastically constrict around sutures 38' when released from device 50 to fixedly attach to the sutures. Alternatively, cuff 54 can be rigid with one suture 38' threaded through the cuff and the other suture 38' around it (FIG. 9f). In any case, when in position close to or against the MSSL, cuff 54 is released from device 50 and device 50 is removed (FIG. 9g). Sutures 38' can then be tied around cuff 54 by running a knot 56 from outside the body to cuff 54 (FIG. 9h).

The proximal end of Mesh 52 can then be secured to anchor sutures using approaches well known in the art.

A s used herein the term "about" refers to ±10%.

Additional objects, advantages, and novel features of the present invention will become apparent to one ordinarily skilled in the art upon examination of the following example, which is not intended to be limiting.

EXAMPLE

Reference is now made to the following example, which together with the above descriptions, illustrate the invention in a non limiting fashion.

A prototype of the device described herein was used in a pelvic repair procedure. Ten female subjects 42 to 76 years of age and having Centro-apical prolapse, were treated using the present device and a suture-anchor or mesh-anchor implant.

Procedure

The patients were anesthetized and the present device was utilized to deliver a suture anchor with or without a mesh to the SSL after a posterior colpotomy and dissection were performed as described hereinabove. The suture was secured with or without a mesh and an initial pull out force was verified by manually pulling on the suture end. The suture end were then attached to the uterine cervix fibrotic ring, the serosa of the vaginal apex, or the utero-sacral ligaments, the vagina (in post hysterectomy subjects), or any other appropriate centro-apical anchoring point of the pelvic floor as is routine for prolapse procedures. Both sutures were tied while lifting prolapsed uterus to its original location. The small colpotomy was then closed to end the procedure.

Two anchors were implanted in each patient (one per side). Two patients were implanted with the suture-anchor and 8 with the suture+mesh anchor. Average procedure time was 30 minutes.

Results

The pelvic organ prolapse quantification (POP-Q) score was 3-4 prior to the procedure. Following the procedure the POP-Q score was 0/1. No device related serious adverse events (SAE) or adverse events (AE) were observed immediately following the procedure. A survey and examination conducted at 3 months post operation, indicated patient satisfaction with no device related AE or complaints from the patients and no recurrence of prolapse.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surgical device comprising:
    an elongate cylindrical housing, adapted for mounting on a finger of a user, said housing having external walls, including a top wall, a bottom wall and first and second side walls, a proximal opening and a distal opening, said distal opening being formed in said bottom wall;
    a rigid tube;
    a tissue repair implant including a tissue anchor mounted on said rigid tube, at least one suture and a suture attachment element; and
    at least one rigid guide tube attached to said housing, along one of said side walls, said at least one guide tube being configured for guiding said tissue repair implant from a proximal opening of said at least one guide tube to a distal opening of said at least one guide tube.

2. The device of claim 1, and wherein said suture attachment element is arranged to constrict around said at least one suture to fixedly attach thereto.

3. The device of claim 1, wherein said at least one guide tube is attached to said housing such that said proximal opening of said at least one guide tube protrudes beyond a proximal end of said elongate cylindrical housing.

4. The device of claim 1, wherein said at least one guide tube is attached to said elongate cylindrical housing such that said proximal opening of said at least one guide tube is positioned above a back of a hand of said user when said elongate cylindrical housing is mounted on said finger of said user.

5. The device of claim 1, wherein said elongate cylindrical housing is configured so as to enable said user to palpate a tissue via said finger, to which said elongate cylindrical housing is attached.

6. The device of claim 5 wherein said at least one guide tube is attached to said elongate cylindrical housing such that said distal opening of said at least one guide tube abuts the tissue when said finger of said user contacts the tissue.

7. The device of claim 5, wherein said at least one guide tube is attached to said elongate cylindrical housing such that said distal opening of said at least one guide tube is displaced from the tissue when said finger of said user contacts the tissue.

8. The device of claim 1, wherein an end of said at least one suture is attached to said tissue anchor.

9. The device of claim 1, wherein said elongate cylindrical housing is configured for enabling flexion of said finger at a distal and/or proximal interphalangeal joint.

10. The device of claim 1, and also comprising an imaging device attached to said elongate cylindrical housing.

11. The device of claim 10, wherein said imaging device is an ultrasound transducer.

12. The device of claim 11, wherein said elongate cylindrical housing is configured such that an imaging head of said ultrasound transducer is capable of abutting a tissue when said ultrasound transducer is attached to said elongate cylindrical housing.

13. The device of claim 12, wherein said imaging head abuts said tissue when said finger attached to said elongate cylindrical housing contacts the tissue.

14. The device of claim 13, wherein the tissue is a posterior-lateral vaginal wall and said elongate cylindrical housing is configured for delivery into a vaginal canal via said finger.

15. The device of claim 14, wherein when said elongate cylindrical housing is positioned within said vaginal canal with said finger in contact with said posterior-lateral vaginal wall, said proximal opening of said at least one guide tube extends out of said vaginal canal.

* * * * *